United States Patent [19]

Diamond et al.

[11] 4,091,324
[45] May 23, 1978

[54] CONDUCTIVITY CELL

[75] Inventors: Joseph M. Diamond, Brooklyn; Joseph T. Kuzmik, Sloatsburg; Horace A. Teass, Jr., Pleasantville, all of N.Y.; Patrick F. McKernan, Middletown, N.J.

[73] Assignee: McNab, Incorporated, Mount Vernon, N.Y.

[21] Appl. No.: 719,598

[22] Filed: Sep. 1, 1976

[51] Int. Cl.² .................................................. G01N 27/42
[52] U.S. Cl. ...................................... 324/30 B; 324/29
[58] Field of Search .................... 324/29, 30 R, 30 B, 324/72.5

[56] References Cited

U.S. PATENT DOCUMENTS

| 2,611,007 | 9/1952 | Cade et al. | 324/30 B |
| 2,687,185 | 8/1954 | McChesney | 324/30 B |
| 3,065,409 | 11/1962 | Estelle | 324/30 B |

Primary Examiner—Rudolph V. Rolinec
Assistant Examiner—Michael J. Tokar
Attorney, Agent, or Firm—Peck & Peck

[57] ABSTRACT

A conductivity cell for measuring the conductivity of a liquid comprising a pair of spaced apart electrodes insulated from each other. The proper spacing of the electrodes is provided by a washer formed of insulating material and it is strong, rigid and highly stable chemically and mechanically and is substantially unaffected by wide temperature variations. A single electric conducting element extends through the cell and at one end is electrically fixed to one of the electrodes. The single electric conducting element is adjustable to maintain the two electrodes and insulating washer in proper position. A protective and insulating shield is provided for detachable connection to the conductivity cell to protect the electrodes.

6 Claims, 9 Drawing Figures

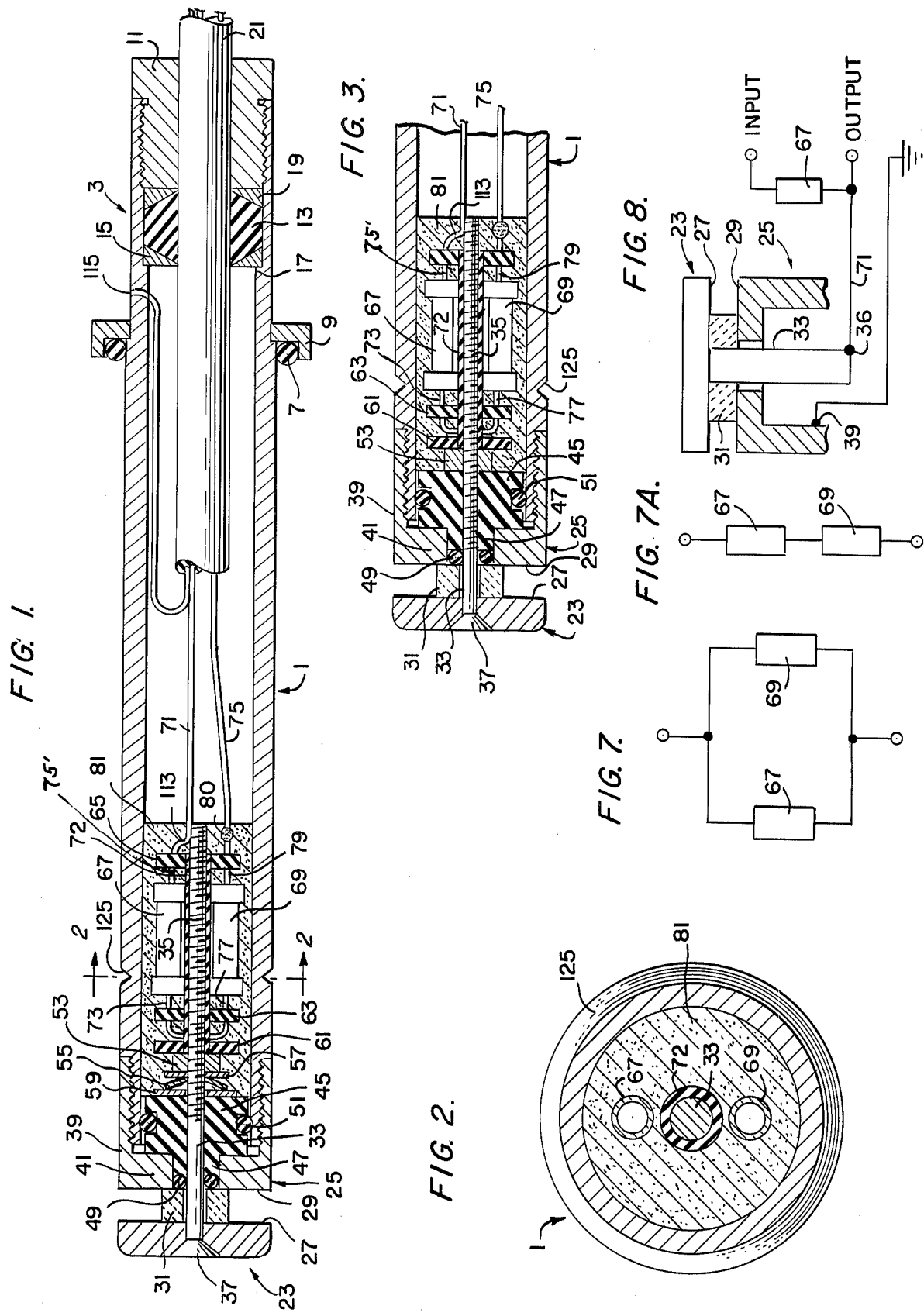

CONDUCTIVITY CELL

BACKGROUND OF THE INVENTION

The present invention is concerned with a conductivity cell which has been designed to support a pair of spaced apart electrodes which may be formed of precious metals, said electrodes being applied in opposing spaced apart positions on two spaced apart metal electrode carrying members. The electrodes and the metal carrying members therefore are retained in a specific spaced apart relation and are insulated from one another by means of an insulating element. The conductivity cell includes one or a plurality of thermistors which are positioned therein in good thermal contact with the surrounding liquid so as to properly sense and compensate for changes in liquid temperature.

It is within our contemplation to provide a protecting and insulating shield covering and protecting at least that portion of the conductivity cell, including the electrodes, which is positioned within the stream of liquid. This protective shield, as will be fully explained hereinafter, is detachably connected to the conductivity cell.

SUMMARY OF THE INVENTION

Conductivity cells are designed to be positioned in a liquid stream in order to measure the electrical conductivity of the stream of liquid. Such conductivity cells provide a pair of electrodes which are positioned in the liquid stream, are spaced apart and must be electrically insulated from each other.

A conductivity cell includes a housing, and in this instance such housing is of metal and within such housing or casing a plurality of elements are disposed for both supporting the electrodes and insulating them from each other. Within the housing, one or a plurality of thermistors are disposed and function to sense and compensate for changes in the temperature of the liquid stream.

One of the significant and major characteristics of the conductivity cell of this invention resides in the means which is disposed between the electrodes and is in contact with them and is formed of a particular material which is strong, is an electrical insulator and is highly stable chemically and mechanically and is importantly substantially unaffected by wide temperature variations. As this description proceeds, it will be evident that since the means is disposed in the liquid stream, the conductivity of which is being measured, the above mentioned characteristics thereof are highly desirable. The separation of the two (2) electrodes is quite important and it is desirable to maintain this separation constant over wide ranges of liquid temperature variation and the means which is used in this conductivity cell due to its stability over wide temperature variations fully serves this requirement.

In addition to the thermistors which are mounted in the housing, a plurality of other elements are mounted therein which serve as insulating and mounting means for the electrodes as well as the spacing means therefore. A unique arrangement has been devised for mounting such various elements and for aiding in the proper spacing of the electrodes. This arrangement is relatively simple and performs its function with few working parts. Such unique arrangement also aids in the assembly of the cell.

This invention also involves protective shielding and insulating means for the electrodes which functions to restrict the measuring current to the liquid stream which is flowing between the electrodes. This shield also keeps the measuring current away from external metal surfaces so that the sensitivity of the cell is made essentially independent of any surrounding surfaces. Mechanical protection of the electrodes while installed in the liquid stream and also when the cell is removed for inspection or the like, is also provided by the shield. Additionally this shield provides protection against electrical shock to the operator removing the cell for inspection and in the event of deterioration of the cell, to the extent that electrode carrying member 23 becomes detached, it will retain the detached piece and prevent it from lodging in the piping system.

Additional objects and advantages of the present invention will become more readily apparent to those skilled in the art when the following general statements and descriptions are read in the light of the appended drawings.

BRIEF DESCRIPTION OF THE DRAWINGS

FIG. 1 is a sectional view through the conductivity cell.

FIG. 2 is a view taken on line 2—2 of FIG. 1.

FIG. 3 is a sectional view of a modified form of conductivity cell, with parts thereof broken away.

FIG. 7 illustrates circuitry for connecting the thermistors in parallel.

FIG. 7A illustrates circuitry for connecting the thermistors in series.

FIG. 8 is a diagrammatic illustration of an electrical diagram embodying all conductivity cells of the general nature of those described herein.

DESCRIPTION OF THE INVENTION

Figure 4:
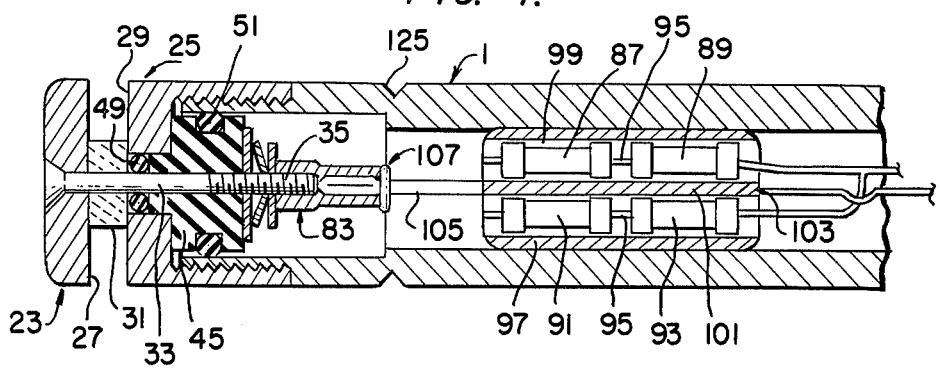
FIG. 4 is a sectional view of a further form of conductivity cell, with parts thereof broken away.

In the accompanying drawings we have used the numeral 1 to designate in its entirety the cell body which is of elongated tubular construction comprising a housing or casing in which are operatively mounted certain of the elements of the conductivity cell. The cell body 1 is formed of metal and, as will become apparent as this description proceeds, provides one of the electrical conducting means of the cell. The cell body or housing comprises a rear portion 3 and a forward portion 5. Adjacent to but forwardly spaced from the rear end of the cell body is an O ring 7, which encircles the cell body, and an O ring stop element 9 which also encompasses the cell body and is fixed thereto and prevents the O ring 7 from rearward movement relative to the cell body. As is well known in this art, the conductivity cell is conventionally used with a valve and the O ring 7 and the O ring stop element 9 affect a liquid tight seal between the conductivity cell and the end wall of such valve. The rear end 3 of the tubular cell body 1 is closed by a hollow gland nut 11 which is threadedly received within the rear end of the cell body. Forwardly of the hollow gland nut 11 is a hollow rubber gasket 13 and a forward ring gasket 15 is in abutment with the rubber gasket 13 and also in abutment at its opposite side with a shoulder 17 formed in the internal circumferential surface of the cell body. A further ring gasket 19 is provided on the opposite side of the rubber gasket 13. Since the elements 11, 13, 15 and 19 are hollow, a cable 21 extends therethrough, all of which comprises conventional construction in conductivity cell of this nature.

The conductivity cell provides a pair of oppositely disposed spaced apart electrode carrying members designated generally by the numerals 23 and 25 and electrodes 27 and 29 forming parallel surfaces are applied on the opposing faces of the electrode carrying members 23 and 25. The electrode carrying member 23 is preferably, though not necessarily, of disc configuration. The essential function of insulation and maintaining the electrodes in the same spaced apart relationship regardless of wide variations in liquid temperature is provided by a ceramic washer, spacer or the like element 31. This ceramic washer 31 provides an accurate and stable means for controlling the electrode separation. It is of substantial significance that this separation remain constant as it controls the electrical sensitivity of the cell, as reflected in the so called "cell constant". It has been our experience that washers 31 which are formed of ceramic materials are exceedingly suitable for this particular usage since such ceramic materials are excellent electrical insulators, are strong, rigid and highly stable chemically and mechanically and are practically unaffected by wide temperature variations.

What we shall term a "through rod" 33 which is formed of metal is provided and a portion thereof, as at 35, is threaded. The through rod 33 at its forward end extends exteriorly of the cell body and permanently mounted on the forward end thereof is the electrode carrying member 23. The electrode carrying member 23 may be permanently and electrically fixed to the end of the through rod 33 in any suitable manner, however, in the drawings such permanent fastening is illustrated as being accomplished by a flared head 37 which rests in a complimentary cavity formed in that electrode carrying member. It will be appreciated that because of this construction, a sound electrical connection is made between the electrode carrying member 23 and its electrode to the through rod 33. It will thus be recognized that we have provided what we shall term a "bolted-up" construction with a rigid, stable insulating separator for the electrodes. This insures an accurately defined and stable value of "cell constant" and obviates the necessity for adjustment of electrode spacing. It will also be clear that the electrode connection from electrode carrying member 23 is carried through the opening in washer 31 by means of the through rod 33.

The other electrode carrying member, which is designated generally by the numeral 25, is of generally cap like configuration providing a rearwardly extending internally threaded skirt 39 having an annulus 41 depending from the forward end thereof. It will be recognized, by consideration of the drawings, that the electrode 29 is applied to the surface of the annulus 41. The rearwardly extending internally threaded skirt portion 39 is adapted to mate with a diametrically reduced portion on the forward end of the cell body which is threaded as at 43. It will thus be appreciated that the cap like electrode carrying member 25 is screwed into operative position on the forward end of the cell body and since the electrode carrying member and the cell body are both comprised of metal, a sound electrical connection between the electrode 29 and the cell body will be made. The annulus 41 provides an opening into the cell body and the through rod 33 extends through this opening and forwardly therebeyond to its fixation on the electrode carrying member 23.

Positioned within the forward end of the cell body 1 is an insulating plug 45 having a forwardly extending portion 47 which extends a distance into the free area between the internal circumferential surface of the annulus 41. An O ring 49 is positioned between the washer 31 and the extending portion 47, and a further O ring 51 is provided which encircles the insulating plug 45. By means of these two O rings 49 and 51, the cell body is sealed against leakage of liquid thereinto.

A nut 53 is threadedly mounted on the threads 35 of the through rod 33 so that the through rod 33 may be pulled up by operation of the nut. We provide one or more tension washers 55 disposed between flat washers 57 and 59, these three washers aid in keeping proper tension on the structure. Obviously the flat washer 57 is in abutment with the nut 53 while the other flat washer 59 is in abutment with the rear surface of the insulating plug 45 and, of course, the through rod extends through these three washers. A pair of thermistor supporting and insulating washers 61 and 63 are disposed in spaced apart relation with the through rod extending therethrough, rearwardly of the nut 53 and a further mounting and insulating washer 65 is positioned with the through rod extending therethrough adjacent to but forwardly removed from the rear end of the rod.

A pair of thermistors 67 and 69 are assembled between the washer 63 and the washer 65. While we illustrate two of such thermistors, this is merely done by way of illustration and not as a limitation, as more than two such thermistors may be used and a conductivity cell including more than two such thermistors will clearly fall within the spirit and scope of this invention. A further mounting and insulating means in the form of insulating tubing 72 enwraps the through rod 33 and extends through washers 61, 63 and 65, or alternately only between washers 63 and 65 and abutting the faces of these washers. The leads 73 and 75' extend from the thermistor 67 while leads 77 and 79 extend from thermistor 69. The leads 75 and 79 are electrically connected as at 80. The mounting and insulating washer 65 is drilled so that leads 75' and 79 may extend therethrough rearwardly, the lead 75' being electrically connected as at 113 to the through rod 33 and also to the rearwardly extending lead 71. The leads 71 and 75 extend to the cable 21. The washer 63 is also drilled to receive therethrough leads 73 and 77. The mounting and insulating washer 61 which is spaced from the washer 63 is not drilled and the leads 73 and 77 are connected together between these washers 61 and 63 as clearly shown in the drawings. It will be appreciated that the insulating tubing 72 which extends through washers 61 and 63 will prevent the leads 73 and 77 from touching through the through rod 33. The washers 61, 63 and 65 and also the insulating tubing or sleeve 72 are preferably made from high quality, high temperature insulating materials such as fluorocarbons. The insulating tubing 72 is relatively thin and has a degree of flexibility and some types which we may use are known as "heat shrink" since the application of heat makes such tubing shrink giving a form fitting covering.

In the assembly of the conductivity cell, the mounting and insulating washers 61, 63 and 65 function not only for the purposes as set forth above, but as temporary insulating supports for the thermistors 67 and 69. This temporary support is accomplished by passing the thermistor leads 73 and 77 through the washer 63 as described above and also the thermistor leads 75' and 79 through washer 65 as described above. After being temporarily supported by the leads in the washers, the thermistors, as well as certain other components of the apparatus, are surrounded and positioned and supported by and within a filler material 81 which is preferably castable providing an excellent electrical insulator and a good thermal conductor and suitable for wide temperature ranges. While we have stated that the washers 61, 63 and 65 serve as temporary supports for the thermistors, it will be appreciated that when the filler material has set, it will function as supporting means for these components, however, the aforesaid washers are not removed but still serve their insulating functions. It will also be evident that the thermistors 67 and 69 are maintained in good thermal contact with the surrounding liquid by means of the filler material 81 and that the thermistors are located close to the electrodes and consequently sense the liquid temperature in the vicinity of said electrodes.

FIG. 3 illustrates a modified form of the invention as disclosed in FIG. 1 and in the description of FIG. 3 the same reference numerals as have been used in the description of FIG. 1 are used in the description of FIG. 3 for similar parts. In this form of the invention we have eliminated the flat washers 57 and 59 and the tension means 55 which are embodied in the form illustrated in FIG. 1. The holding function of these eliminated elements is taken over by the insulating plug 45 which is threaded internally for this purpose and is screwed directly on to the through rod 33. It will be observed that in FIG. 3 the through rod 33 is provided with threads along a greater distance thereof than in FIG. 1.

Figure 5:
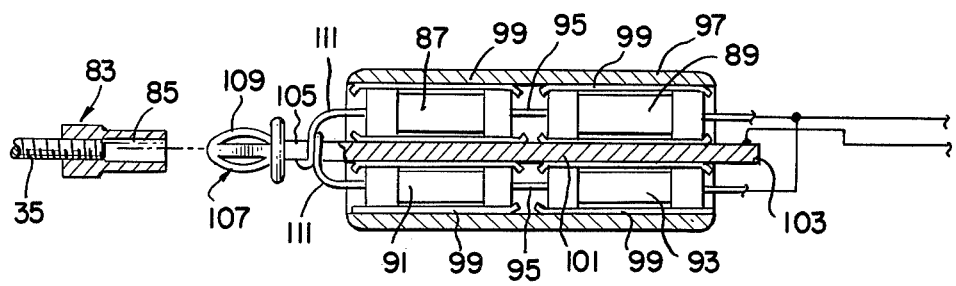
FIG. 5 is a detailed view illustrating the cartridge for the plurality of thermistors as illustrated in FIG. 4, and also illustrating a type of detachable electrical plug allowing the thermistor cartridge to be plugged into the conductivity cell.

In FIGS. 4 and 5 of the drawings a further form of the invention is illustrated and again in the description of FIGS. 4 and 5 the same reference numerals will be used for similar parts as have been used in the description of FIG. 1.

The form of the invention illustrated in FIG. 4 provides a rearwardly extending socket extension designated in its entirety by the numeral 83. This rearwardly extending extension is threaded or otherwise affixed to the rear end of the through rod 33 and extends rearwardly from this point of fixation providing a socket member 85. In this modification, we provide four thermistors 87, 89, 91 and 93 having the usual leads 95 extending therefrom and being connected in series—parallel. That is the series connected pair of thermistors 87 and 89 is in parallel with the series connected pair 91 and 93. While four of such thermistors are shown in FIG. 4, it is to be understood that more or a lesser number may be used. The lead connections and electrical circuitry per se form no part of the inventive subject matter of this invention. In other words, any necessary electrical connections to the electrodes and the thermistors are made by means of wire leads and/or structural parts of the cell body (such as by means of the through rod 33 and the cell body) as required and convenient.

The four thermistors are mounted in a separate metal housing or cartridge 97 which as will become apparent, is adapted to be mounted within the cell body or housing 1 with a snug fit. In order to prevent electrical contact between the cartridge 97 and the thermistors, insulating sleeves 99 are provided. Extending through and between the sets of thermistors is a relatively rigid conducting rod 101 which extends a distance rearwardly of the cartridge as at 103 and extends forwardly beyond the cartridge as at 105. On the forward end of the portion 105 of the conductor 101 is an electric connecting means generally designated by the numeral 107 which consists of a plurality of flexible metal members 109 which are outwardly flexed in non-conducting position as illustrated in FIG. 5 of the drawings. This structure 107 is inserted into socket member 85 thereby inwardly flexing the members 109 producing a sound electrical connection between electrode carrying member 23, through rod 33 and conductor 101. This electrical connecting means is known in this discipline as a "banana plug" and it will be appreciated that this arrangement permits the complete cartridge 97 to be plugged into the finished conductivity cell. Leads 111 are provided from the thermistors and are electrically connected through conductor 101 with the electrode carrying member 23 and its electrode 27. While the electric circuitry which may be used in this conductivity cell, is not per se, a part of this invention, it is to be noted that (referring to FIG. 1) the lead 75' is connected to the through rod 33, as at 113, providing an output connection while the common connection is made at 115 with the metallic cell body conductor member.

The present conductivity cell which readily permits the use of more than one thermistor, and offers a number of advantages, including improved thermal contact due to increased area, and the possibility of greatly increased accuracy of thermistor value. Thermistors are not normally available from manufacturers with high accuracy, but when more than one are connected together in series or parallel, a much more accurate value may be obtained by sorting and pairing. For example, if a value of 5000 ohms is desired, then this value may be achieved by connecting two 2500 ohm thermistors in series (or two 10,000 ohm thermistors in parallel). If one thermistor is somewhat high in value, it may be paired with a thermistor which is somewhat low in value. While it is unlikely that exactly 5000 ohms will be achieved in this way, it is clear that a considerable improvement may be made.

Figure 6:
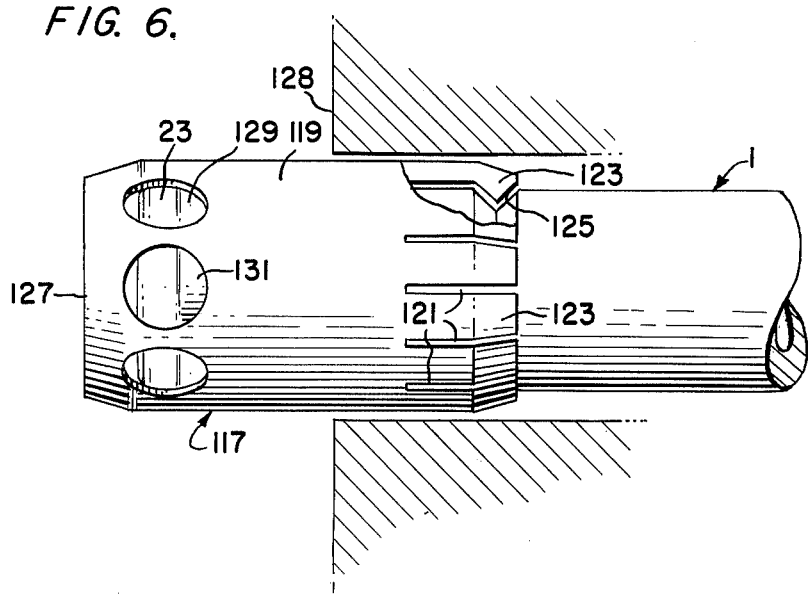
FIG. 6 is a plan view of a conductivity cell, with parts thereof broken away and illustrating the protecting and insulating shield for the electrodes, the conductivity cell with the protecting and insulating shield thereon is illustrated inserted in a cell mount, for illustrative and descriptive clarity the spacing between the cell mount and the protecting and insulating shield is shown as somewhat enlarged, actually a snug fit is provided between the mount and the cell.

FIG. 6 illustrates a protective insulating shield which we have designated generally by the numeral 117. This shield is adapted to be removably attached to at least that portion of the conductivity cell which extends into the liquid stream, the conductivity of which is being measured. The insulating and protective shield 117 comprises a somewhat elongated body 119, the internal diameter of which is more or less the same as the external diameter of the cell body 1. The rearward end of the body 119 is provided with a circumferential series of slits 121 which are circumferentially spaced apart providing a plurality of attaching fingers 123 which when the shield is in operative insulating and protective position on the cell body snap into a circumferential groove 125 which is formed in the cell body 1. Adjacent to but rearwardly removed from the forward end 127 of the shield, we provide a circumferential series of spaced apart apertures 129 which, when the shield is in operative protecting and insulating position, extend over the electrode carrying member 23 so as to permit the liquid stream to flow through the shield in contact with both electrodes and their carrying members 23 and 25. The shield 117 is positioned in its proper operating position on the conductivity cell when the cell is removed from the cell mount 128, the shield being slid on and over the forward end of the cell until the fingers 123 snap into the circumferential groove 125. With the protective shield mounted on the cell as described, the cell is positioned within the cell mount 128 so that the insulating and protective shield is positively locked to the shield, as the mount fits snugly enough to prevent fingers 123 from retracting from groove 125. It will be recognized, particularly upon consideration of FIG. 6, that the shield does not restrict the flow of the liquid stream between the electrodes.

What is claimed is:

1. A conductivity cell for measuring the conductivity of a liquid stream comprising:
   a generally elongated housing;
   a plurality of cell components mounted in said housing;
   a pair of spaced apart electrodes extending axially from said housing and adapted to be inserted in the liquid stream;
   insulating and spacing means positioned between said electrodes and in contact therewith to insulate said electrodes from each other and to maintain them in stable axially spaced apart relationship;
   an electrical conducting element mounted within said housing and extends therefrom and electrically connected and fixed to one of said electrodes;
   said other electrode being mounted on said housing and insulated from said electrical conducting elements;
   said electric conducting element being operable to maintain said one of said electrodes in engagement with said insulating and spacing means, and to maintain said insulating and spacing means in engagement with said other electrode;
   said insulating and spacing means is of rigid construction and is characterized by being formed of a ceramic material having good electrical insulation qualities, is strong and highly stable chemically and mechanically and is substantially unaffected by wide temperature variations to maintain and control the spaced apart relationship of the electrodes.

2. A conductivity cell for measuring the conductivity of a liquid stream comprising:
   a housing, a portion of which is adapted to be inserted in said liquid stream;
   a plurality of cell components mounted in said housing;
   a pair of spaced apart electrodes extending from said housing and adapted to be inserted in the liquid stream;
   insulating and spacing means positioned between said electrodes and in contact therewith to insulate said electrodes from each other and to maintain them in stable spaced apart relationship;
   means fixed and electrically connected to one of said electrodes;
   said other electrode being removably mounted on said housing and insulated from said means;
   a protective and insulating sleeve removably mounted on and extending from an end of said housing and extending around said electrodes and being provided with a series of apertures therein adjacent said electrodes whereby the liquid stream may pass through the protective and insulating sleeve and around said electrodes.

3. A conductivity cell for measuring the conductivity of a liquid stream comprising:
   a housing, a portion of which is adapted to be inserted in said liquid stream;
   a plurality of cell components mounted in said housing;
   a pair of spaced apart electrodes extending from said housing and adapted to be inserted in the liquid stream;
   insulating and spacing means positioned between said electrodes and in contact therewith to insulate said electrodes from each other and to maintain them in stable spaced apart relationship;
   means fixed and electrically connected to one of said electrodes;
   said other electrode being removably mounted on said housing and insulated from said means;
   a protective and insulating sleeve removably mounted on and extending from an end of said housing and extending around said electrodes and being provided with a series of apertures therein adjacent said electrodes whereby the liquid stream may pass through the protective and insulating sleeve and around said electrodes
   and said sleeve is formed of a material having a degree of flexibility and is provided with a forward end in which said apertures are formed and a rearward end which is provided with fingers detachably connected to said housing.

4. The invention as recited in claim 3, wherein a circumferential groove is provided in said housing and said fingers removably extend into said groove.

5. The invention as recited in claim 4, wherein a cell mount is provided and said conductivity cell with the protecting and insulating sleeve mounted thereon is inserted in said cell mount with a relatively snug fit.

6. The invention as recited in claim 5, wherein said fingers are in substantial engagement with said cell mount to positively maintain and lock said fingers in said circumferential groove while said conductivity cell is in inserted position within said cell mount.

* * * * *